(12) United States Patent
Fischvogt et al.

(10) Patent No.: US 8,114,053 B2
(45) Date of Patent: Feb. 14, 2012

(54) PORT FIXATION WITH INTERLOCKING STRUCTURE

(75) Inventors: Gregory Fischvogt, Hamden, CT (US); Michael Bettuchi, Middletown, CT (US); Matthew D. Cohen, Berlin, CT (US); Eric Taylor, Hampton, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 247 days.

(21) Appl. No.: 12/487,071

(22) Filed: Jun. 18, 2009

(65) Prior Publication Data

US 2010/0016798 A1 Jan. 21, 2010

Related U.S. Application Data

(60) Provisional application No. 61/081,466, filed on Jul. 17, 2008.

(51) Int. Cl.
*A61M 5/178* (2006.01)
(52) U.S. Cl. .................................. 604/164.01
(58) Field of Classification Search ............ 604/164.01, 604/164.07, 164.11, 165.01, 165.04, 167.05; 606/108
See application file for complete search history.

(56) References Cited

U.S. PATENT DOCUMENTS

| | | | |
|---|---|---|---|
| 5,312,363 | A | 5/1994 | Ryan et al. |
| 5,549,565 | A | 8/1996 | Ryan et al. |
| 5,735,867 | A | 4/1998 | Golser et al. |
| 5,830,195 | A | 11/1998 | Peters et al. |
| 2006/0189999 | A1 | 8/2006 | Zwirkoski |
| 2008/0171984 | A1 | 7/2008 | Miller |
| 2009/0182282 | A1 | 7/2009 | Okihisa et al. |

FOREIGN PATENT DOCUMENTS

WO 2007118070 10/2007

OTHER PUBLICATIONS

European Search Report, Application No. 09 25 1791, dated Oct. 19, 2009.

*Primary Examiner* — Nicholas Lucchesi
*Assistant Examiner* — Brooke Matney

(57) ABSTRACT

The present disclosure relates to a surgical access system that includes a cannula assembly adapted for removable positioning within a percutaneous tissue tract, and an obturator assembly removably positionable within the cannula assembly. The cannula assembly includes a cannula housing, a cannula sleeve, and first engagement structure, and the obturator assembly includes an obturator housing, an obturator sleeve, and second engagement structure. The first engagement structure and the second engagement structure are correspondingly dimensioned such that rotation of the obturator assembly in a first direction effectuates corresponding rotation of the cannula assembly to facilitate advancement of the cannula assembly through tissue.

23 Claims, 9 Drawing Sheets

# PORT FIXATION WITH INTERLOCKING STRUCTURE

CROSS REFERENCE TO RELATED APPLICATION

The present application claims the benefit of and priority to U.S. Provisional Application Ser. No. 61/081,466 filed on Jul. 17, 2008, the entire contents of which are incorporated herein by reference.

BACKGROUND

1. Technical Field

The present disclosure relates to surgical devices. More particularly, the present disclosure relates to surgical access systems and methods of using the same during minimally invasive surgical procedures.

2. Background of the Related Art

Minimally invasive surgical procedures, which include both endoscopic and laparoscopic procedures, permit surgery to be performed on target tissue, such as organs, vessels, or the like, at a surgical worksite removed from an opening in the patient's tissue. Such procedures are typically performed through a surgical access system including, among other things, a cannula assembly and an obturator assembly positionable therein.

Generally, in laparoscopic procedures, the surgical worksite is first insufflated to provide increased access to the target tissues. Subsequently, the obturator assembly, which typically includes a distal end adapted to penetrate the patient's tissue, is inserted into the cannula assembly and is used to create a temporary tissue tract. The cannula assembly is subsequently advanced through the tissue tract, thereafter remaining in place, and the obturator assembly is removed such that additional instrumentation can be inserted through the cannula assembly to carry out the remainder of the procedure.

Known surgical access systems are usually pushed through the tissue tract by applying an axial, distally directed force to the surgical access system. Advancing the surgical access system in this manner, however, may unnecessarily stress, stretch, or deform the patient's tissue. Accordingly, it would be desirable to provide a surgical access system that can be advanced through a patient's tissue in a less traumatic manner.

SUMMARY

In one aspect of the present disclosure, a surgical access system is disclosed that includes a cannula assembly adapted for removable positioning within a percutaneous tissue tract, and an obturator assembly removably positionable within the cannula assembly. The cannula assembly includes a cannula housing, a cannula sleeve, and first engagement structure, and the obturator assembly includes an obturator housing, an obturator sleeve, and second engagement structure. The first engagement structure and the second engagement structure are correspondingly dimensioned such that rotation of the obturator assembly in a first direction effectuates corresponding rotation of the cannula assembly to facilitate advancement of the cannula assembly through tissue. It is envisioned that the first engagement structure may depend proximally from the cannula housing and that the second engagement structure may depend distally from the obturator housing.

In one embodiment of the surgical access system, the first engagement structure includes a first plurality of teeth and the second engagement structure includes a second plurality of teeth. The first plurality of teeth is configured and dimensioned for engagement with the second plurality of teeth in an interlocking arrangement. Specifically, each tooth in the first plurality of teeth includes a first inner surface and a first outer surface, and each tooth in the second plurality of teeth includes a second inner surface and a second outer surface, wherein the first outer surface is configured and dimensioned to engage the second inner surface, and the first inner surface is configured and dimensioned to engage the second outer surface. The first outer surface and the second inner surface are each substantially planar such that rotation of the obturator assembly relative to the cannula assembly is substantially restricted in the first direction, and the first inner surface and the second outer surface are correspondingly chamfered such that the obturator assembly is permitted to rotate relative to the cannula assembly in a second direction that is opposite to the first direction.

The cannula sleeve may include a threaded portion that is configured and dimensioned to engage the tissue as the cannula assembly is rotated in the first direction to thereby facilitate advancement of the cannula assembly through the tissue. Additionally, or alternatively, the obturator assembly may include a handle that is configured and dimensioned for manual engagement to facilitate rotation of the obturator assembly.

In one embodiment of the surgical access system, the first engagement structure is defined by an internal configuration of a non-circular opening extending through the cannula housing, and the second engagement structure is defined by an outer configuration of the obturator sleeve. In this embodiment, at least a portion of the obturator sleeve defines a cross-sectional configuration corresponding to the cross-sectional configuration of the opening in the cannula housing such that relative rotation between the obturator assembly and the cannula assembly is substantially restricted.

In an alternative embodiment of the surgical access system, the first engagement structure is defined by an internal configuration of the cannula sleeve and the second engagement structure is defined by an outer configuration of the obturator sleeve. In this embodiment, at least a portion of the obturator sleeve defines an outer cross-sectional configuration that corresponds to an internal cross-sectional configuration of the cannula sleeve, wherein the outer cross-sectional configuration of the obturator sleeve and the internal cross-sectional configuration of the cannula sleeve are non-circular such that relative rotation between the obturator assembly and the cannula assembly is substantially restricted.

In another embodiment of the surgical access system, the first engagement structure includes a rack and the second engagement structure includes a pawl. The pawl is configured and dimensioned for engagement with the rack to permit ratcheting movement of the obturator assembly relative to the cannula assembly. The rack and the pawl may be positioned in any suitable location. For example, the rack may be positioned on an inner wall of the cannula housing, depending inwardly therefrom, and the pawl may be positioned in mechanical cooperation with the obturator sleeve.

The rack includes a plurality of teeth each having a first planar surface and a first chamfered surface, and the pawl includes a second planar surface and a second chamfered surface. The first planar surface of the rack is configured and dimensioned to engage the second planar surface of the pawl such that rotation of the obturator assembly relative to the cannula assembly is substantially restricted in a first direction, and the first chamfered surface of the rack is configured and dimensioned to engage the second chamfered surface of the pawl such that the obturator assembly is permitted to rotate relative to the cannula assembly in a second direction that is opposite to the first direction. The obturator assembly may further include a biasing mechanism connected to the pawl to facilitate reciprocal movement of the pawl in the first and second directions.

In an alternate aspect of the present disclosure, a method of establishing percutaneous access to a surgical worksite is disclosed. The method includes the steps of providing a cannula assembly adapted for removable positioning within a tissue tract, providing an obturator assembly removably positionable within the cannula assembly, positioning the obturator assembly within the cannula assembly, and rotating the obturator assembly in a first direction. The cannula assembly includes first engagement structure and the obturator assembly includes second engagement structure. The first engagement structure corresponds in configuration to the second engagement structure such that rotation of the obturator assembly in the first direction effectuates corresponding rotation of the cannula assembly to facilitate advancement of the cannula assembly through tissue.

These and other features of the surgical access system disclosed herein, and methods of using the same, will become more readily apparent to those skilled in the art from the following detailed description of various embodiments of the present disclosure.

BRIEF DESCRIPTION OF THE DRAWINGS

Various embodiments of the present disclosure are described herein below with references to the drawings, wherein.

DETAILED DESCRIPTION OF THE EMBODIMENTS

Figure 1:
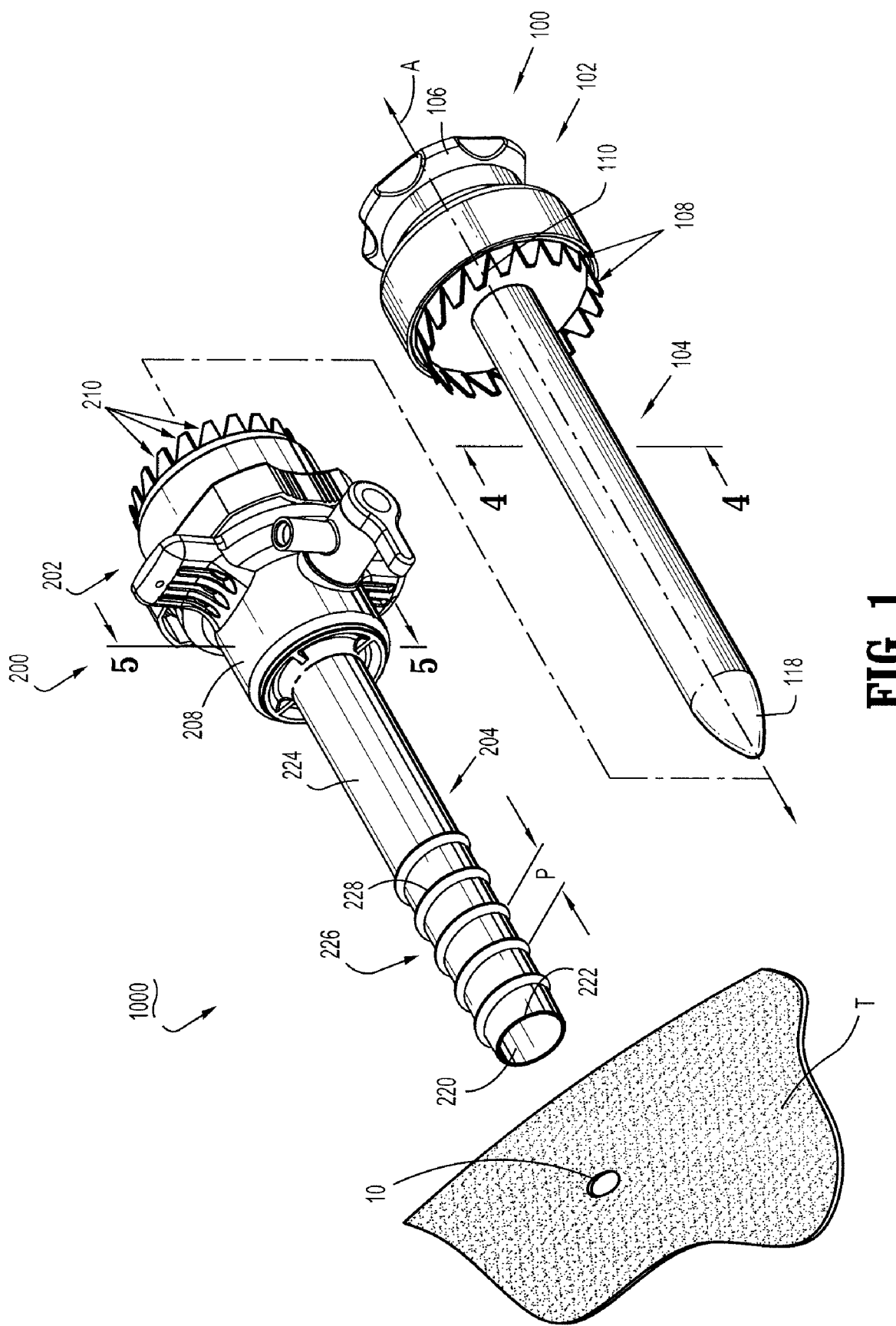
FIG. 1 is a perspective view of a surgical access system in accordance with the principles of the present disclosure shown in a disassembled condition and including an obturator assembly removably positionable within a cannula assembly.

In the drawings and in the description which follows, in which like reference numerals identify substantially similar or identical elements, the term "proximal" will refer to the end of the presently disclosed surgical access system which is closest to the clinician during use, while the term "distal" will refer to the end which is furthest from the clinician, as is traditional and known in the art.

Referring now to the drawings, FIG. 1 illustrates a surgical access system 1000 in general accordance with the principles of the present disclosure. Surgical access system 1000 includes an obturator assembly 100 positionable within a cannula assembly 200.

Figure 2:
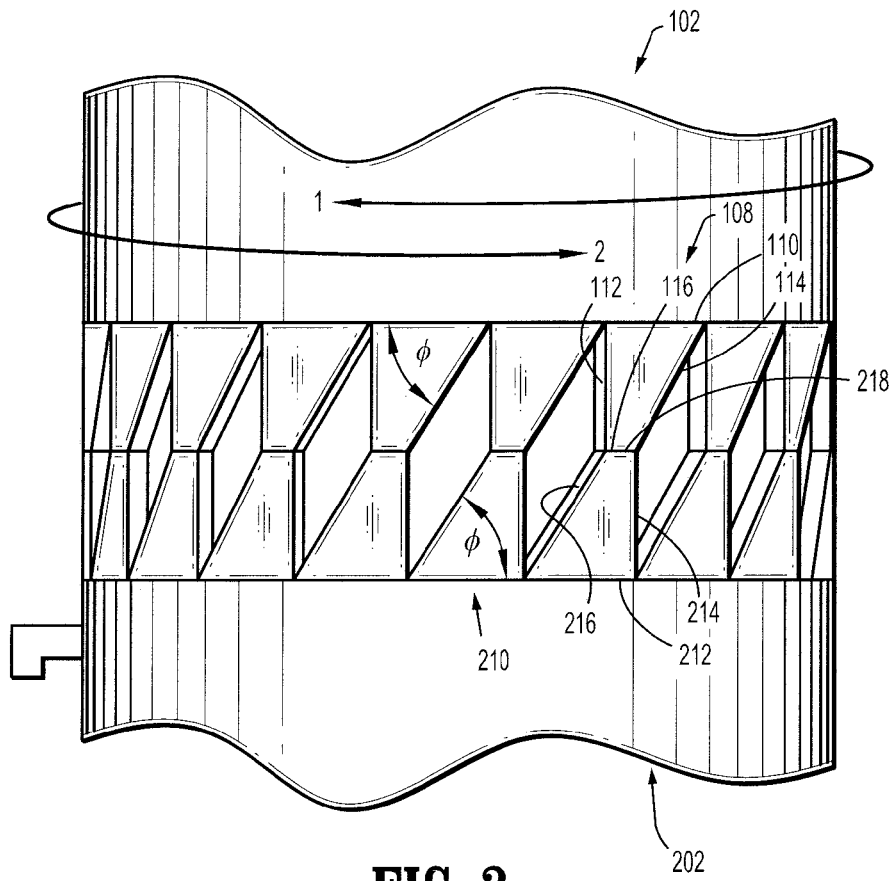
FIG. 2 is an enlarged, side view of the surgical access system of FIG. 1 shown in an assembled condition and illustrating a plurality of teeth formed on each of the obturator and cannula assemblies.
Figure 3:
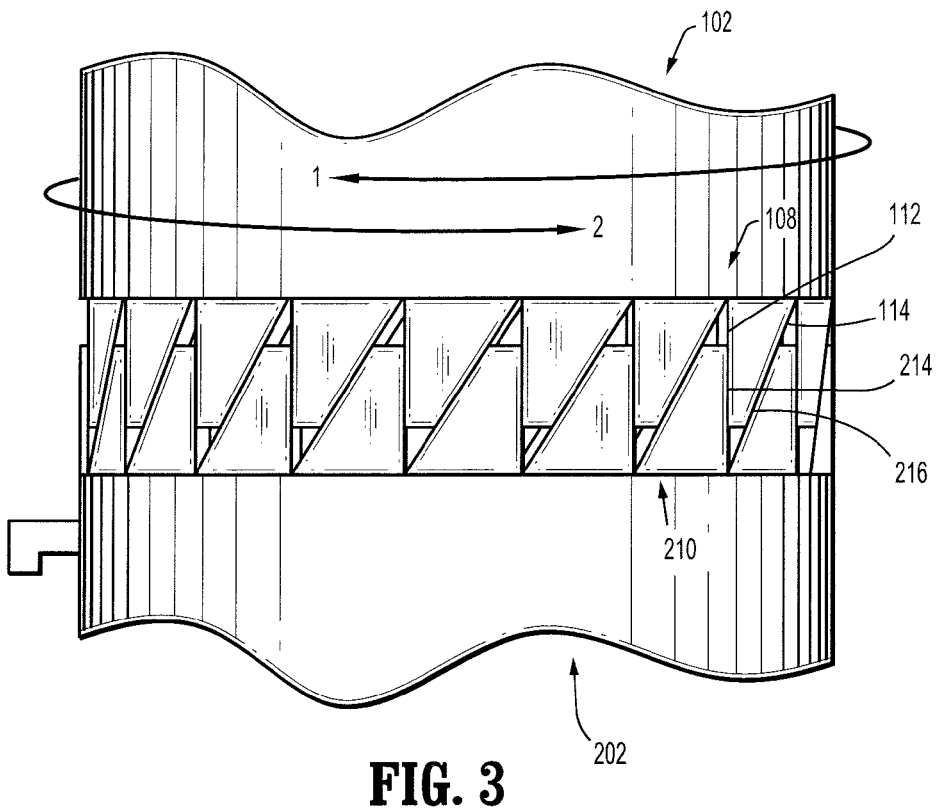
FIG. 3 is an enlarged, side view of the surgical access system of FIG. 1 shown in an assembled condition with the plurality of teeth formed on the obturator and cannula assemblies interlocked such that the obturator and cannula assemblies are in secure engagement.

Obturator assembly 100 includes an obturator housing 102 and an elongate obturator sleeve 104. The obturator housing 102 may include a gripping portion 106 to facilitate manual manipulation of the obturator housing 102 by a clinician. Referring now to FIGS. 2-3 as well, the obturator housing 102 further includes a plurality of teeth 108 depending downwardly (distally) from a distal wall 110. Each of the plurality of teeth 108 includes an inner surface 112 and a chamfered outer surface 114 connected by a substantially planar distal surface 116. The respective inner and outer surfaces 112, 114 of the teeth 108 are each connected to the distal wall 110 of the obturator housing 102, and in the particular embodiment seen in FIGS. 2-3, the inner surface 112 extends from the distal wall 110 in substantially orthogonal relation while the outer surface 114 extends from the distal wall 110 such that an acute angle $\Phi$ is defined therewith.

Figure 4:
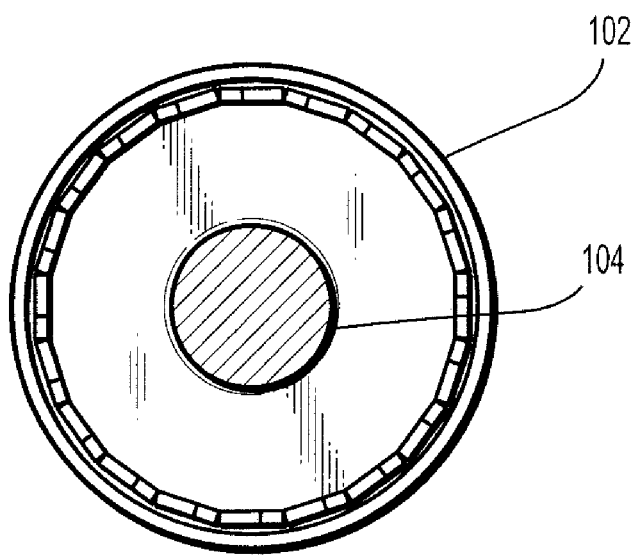
FIG. 4 is a bottom view of the obturator assembly seen in FIG. 1 taken through line 4-4.

The obturator sleeve 104 is coupled to, and extends distally from the obturator housing 102 along a longitudinal axis "A". In one embodiment, as seen in FIGS. 1 and 4, the obturator sleeve 104 defines a substantially circular cross-section along its entire length. However, in alternate embodiments, the obturator sleeve 104 may define a cross-section having other geometrical configurations, as discussed in further detail below.

The obturator sleeve 104 includes a distal end 118 that is adapted to penetrate tissue. In the embodiment of the surgical access system 1000 illustrated in FIG. 1, the distal end 118 of the obturator sleeve 104 defines a substantially blunt, conical configuration such that the obturator assembly 100 is employable to enlarge a pre-existing tissue tract 10 formed in a patient's tissue "T", such as incision created through the use of a scalpel. In alternate embodiments, however, the distal end 118 of the obturator sleeve 104 may be substantially incisive such that the obturator assembly 100 may be used to create the tissue tract 10.

The obturator housing 102 and/or the obturator sleeve 104 may be fabricated from any suitable biocompatible material including metals or polymers, and in alternate embodiments, may be wholly or partially formed of materials that are transparent to permit the visualization of the tissue "T" therethrough during insertion.

Figure 5:
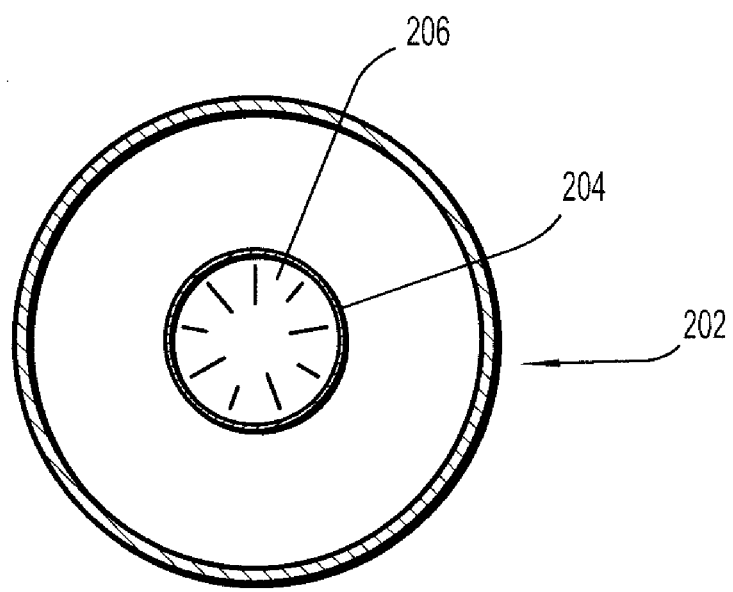
FIG. 5 is a top view of the cannula assembly seen in FIG. 1 taken through line 5-5.

Referring still to FIG. 1, the cannula assembly 200 will be discussed. The cannula assembly 200 includes a cannula housing 202 and an elongate cannula sleeve 204. As seen in FIG. 5, the cannula housing 202 defines an opening 206 therethrough that is configured and dimensioned to permit the passage of one or more surgical instruments, including but not limited to the obturator assembly 100, an endoscope, and/or a surgical fastener applying apparatus. In the embodiment seen in FIGS. 1 and 5, the opening 206 defines a substantially circular configuration, e.g., to accommodate the substantially circular cross-sectional configuration of the obturator sleeve 104. However, in alternate embodiments, the opening 206 may define other geometrical configurations, as discussed in further detail below.

To prevent the passage of insufflation gas through the cannula assembly 200, e.g., through the opening 206 in the cannula housing 202, the cannula housing 202 may include a seal assembly 208 with an internal seal or valve (not shown) that is adapted to close in the absence of a surgical instrument and to form a substantially fluid-tight seal therewith upon insertion, such as a duck-bill or other zero closure valve, to substantially prevent the escape of insufflation gases through the cannula assembly 200. An example of one such internal seal or valve is disclosed in commonly assigned U.S. Pat. No. 5,820,600 to Carlson, et al., which issued Oct. 13, 1998, the entire contents of which are incorporated by reference herein. The present disclosure contemplates that the seal assembly 208 may be either releasably of fixedly connected to the cannula housing 202. Means for releasably connecting the seal assembly 208 to the cannula housing 202 may include a bayonet coupling, threaded connection, latch, friction fit, tongue and groove arrangements, snap-fit, etc.

Referring now to FIGS. 1-3, the cannula housing 202 further includes a plurality of teeth 210 that are configured and dimensioned to engage the teeth 108 of the obturator assembly 100 such that the obturator assembly 100 is selectively engagable with, and disengageable from, the cannula assembly 200.

Each tooth 210 depends upwardly (proximally) from a proximal wall 212 of the cannula housing 202 and includes an outer surface 214 and a chamfered inner surface 216 connected by a substantially planar proximal surface 218. The respective outer and inner surfaces 214, 216 of the teeth 210 are each connected to the proximal wall 212 of the cannula housing 202, and in the particular embodiment seen in FIGS. 2-3, the outer surface 214 extends from the proximal wall 212 in substantially orthogonal relation while the inner surface 216 extends from the proximal wall 212 to define the acute angle Φ therewith, i.e., the same acute angle Φ defined between the outer surface 114 of each tooth 108 formed on the obturator housing 102 and the distal wall 110 thereof.

The cannula sleeve 204 of the cannula assembly 200 extends distally from the cannula housing 202 and defines an internal longitudinal lumen 220 that corresponds in configuration to the obturator sleeve 104 of the obturator assembly 100. Accordingly, in the embodiment of the surgical access system seen in FIG. 1, the cannula sleeve 204, and thus the lumen 220, also defines a circular cross-sectional configuration. The lumen 220 is dimensioned such that the obturator assembly 100, as well as additional surgical instruments including but not being limited to endoscopes and/or surgical fastener applying apparatus, may be positioned therein. In general, the lumen 220 will define an internal dimension substantially within the range of about 4.5 mm to about 15 mm, although a cannula sleeve 204 having a substantially larger or smaller internal dimension is also within the scope of the present disclosure. The cannula sleeve 204 terminates in an open distal end 222 to permit the obturator assembly 100 and/or the additional surgical instruments to pass through the cannula assembly 200.

Figure 6:
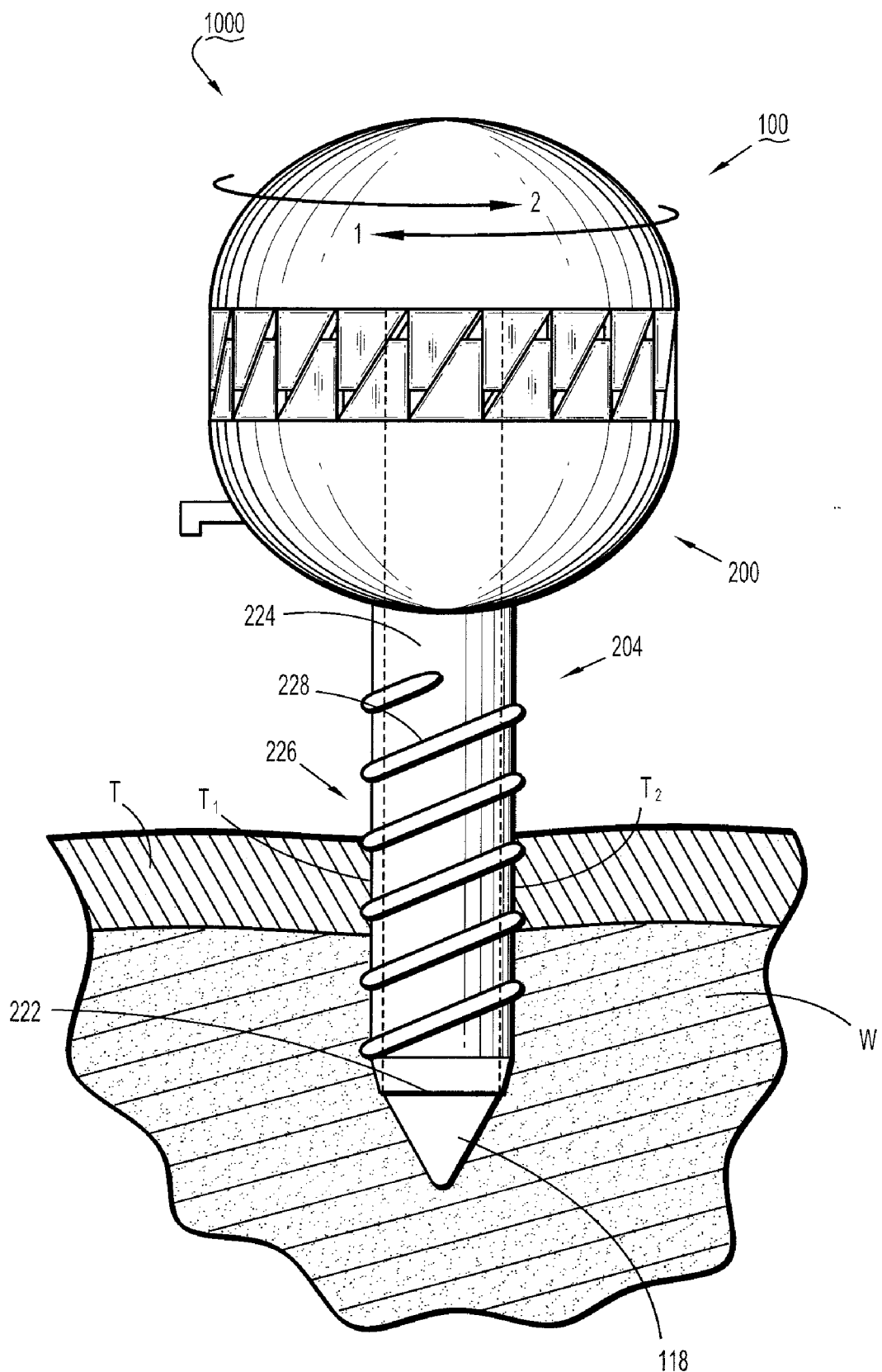
FIG. 6 is a side view of the surgical access system of FIG. 1 in an assembled condition and inserted within tissue.

Referring now to FIGS. 1 and 6, in one embodiment, the cannula sleeve 204 includes an outer wall 224 with a threaded portion 226. The threaded portion 226 includes a plurality of threads 228 arranged to define a pitch "P" that facilitates engagement of the threaded portion 226 and the patient's tissue "T". Engagement of the threaded portion 226 with the tissue "T" facilitates advancement of the cannula assembly 200 through the tissue tract 10 in the manner discussed in further detail below. An embodiment of the cannula assembly 200 having a cannula sleeve 204 with a substantially smooth outer wall 224, e.g., an outer wall 224 that is devoid of the threaded portion 226 seen in FIGS. 1 and 5, however, is not beyond the scope of the present disclosure, however.

The cannula housing 202 and/or the cannula sleeve 204 may be fabricated from any suitable biocompatible material including metals or polymers, and in alternate embodiments, may be wholly or partially formed of materials that are transparent to permit the visualization of the tissue "T" therethrough during insertion.

Referring now to FIGS. 1-3 and 6, a method of using the surgical access system 1000 to provide percutaneous access to a surgical worksite "W" through a patient's tissue "T" will be discussed. Initially, the surgical access system 1000 is assembled by inserting the obturator assembly 100 into the cannula assembly 200. As seen in FIG. 6, the obturator assembly 100 is dimensioned such that the distal end 118 thereof extends beyond the distal end 222 of the cannula sleeve 204 upon insertion.

The obturator assembly 100 is then rotated in the direction of arrow 1 to ensure that the respective teeth 108, 210 formed on the obturator and cannula assemblies 100, 200 are interlocked such that the obturator assembly 100 and the cannula assembly 200 are securely engaged. Interlocking of the teeth 108, 210 can be seen in transition between FIGS. 2 and 3. When the teeth 108, 210 are interlocked, the inner and outer surfaces 112, 114 of each tooth 108 formed on the obturator housing 102 respectively engage the outer and inner surfaces 214, 216 of adjacent teeth 210 formed on the cannula housing 202.

The distal end 118 of the obturator sleeve 104 of the obturator assembly 100 is then positioned within the tissue tract 10 to enlarge the opening defined thereby and thus facilitate insertion of the assembled surgical access system 1000 into the tissue "T".

The engagement between the inner surfaces 112 of the teeth 108 and the outer surfaces 214 of the teeth 210 prohibits relative rotation between the obturator assembly 100 and the cannula assembly 200 in the direction of arrow 1. However, the engagement between the chamfered outer surfaces 114 of the teeth 108 and the chamfered inner surfaces 216 of the teeth 210 creates a camming effect by which the outer surfaces 114 of the teeth 108 traverse the inner surfaces 216 of the teeth 210, thereby permitting relative rotation between the obturator assembly 100 and the cannula assembly 200 in the direction of arrow 2. Consequently, rotation of the obturator assembly 100 in the direction of arrow 1 effectuates corresponding rotation of the cannula assembly 200. In contrast, however, as the obturator assembly 100 in rotated in the direction of arrow 2, the position of the cannula assembly 200 remains substantially constant. This facilitates manipulation of the assembled surgical access system 1000 in a ratcheting manner in which rotation of the obturator assembly 100, and consequently, rotation of the cannula assembly 200, is alternated between the directions indicated by arrows 1 and 2.

As the cannula assembly 200 rotates in the direction of arrow 1, the threaded portion 226 of the cannula sleeve 204 engages the adjacent tissue portions $T_1$, $T_2$ (FIG. 6) defining the tissue tract 10 formed in the tissue "T", thereby advancing the surgical access system 1000 into the tissue "T". Accordingly, the surgical access system 1000 is advanced into and through the tissue "T" solely through the rotation of the obturator housing 100, thereby obviating the need to apply what would be an otherwise requisite axial force in the distal direction and substantially minimizing any unnecessary stressing, stretching, or deformation of the tissue "T".

While a clinician may choose to manipulate the surgical access system 1000 in the ratcheting manner described above, alternating rotation of the obturator assembly 100 between the directions indicated by arrows 1 and 2, in an another method of use, the clinician may choose to simply rotate the obturator assembly 100, and thus the cannula assembly 200, continuously in the direction of arrow 1.

After the cannula assembly 200 has passed through the tissue tract 10 and been securely positioned within the tissue "T", the obturator assembly 100 is withdrawn therefrom such that additional surgical instrumentation can be subsequently inserted through the cannula assembly 200 and into the surgical worksite "W" (FIG. 6) to carry out the remainder of the minimally invasive surgical procedure.

It should be appreciated that, while the above-described methods relate to the insertion of an obturator assembly 100 having a substantially blunt distal end 118 into a pre-existing tissue tract 10 formed in the tissue "T", alternate methods of using the surgical access system 1000 are also contemplated in which the obturator assembly 100 includes a substantially incisive distal end 118 that is employable to create the tissue tract 10.

Figure 7:
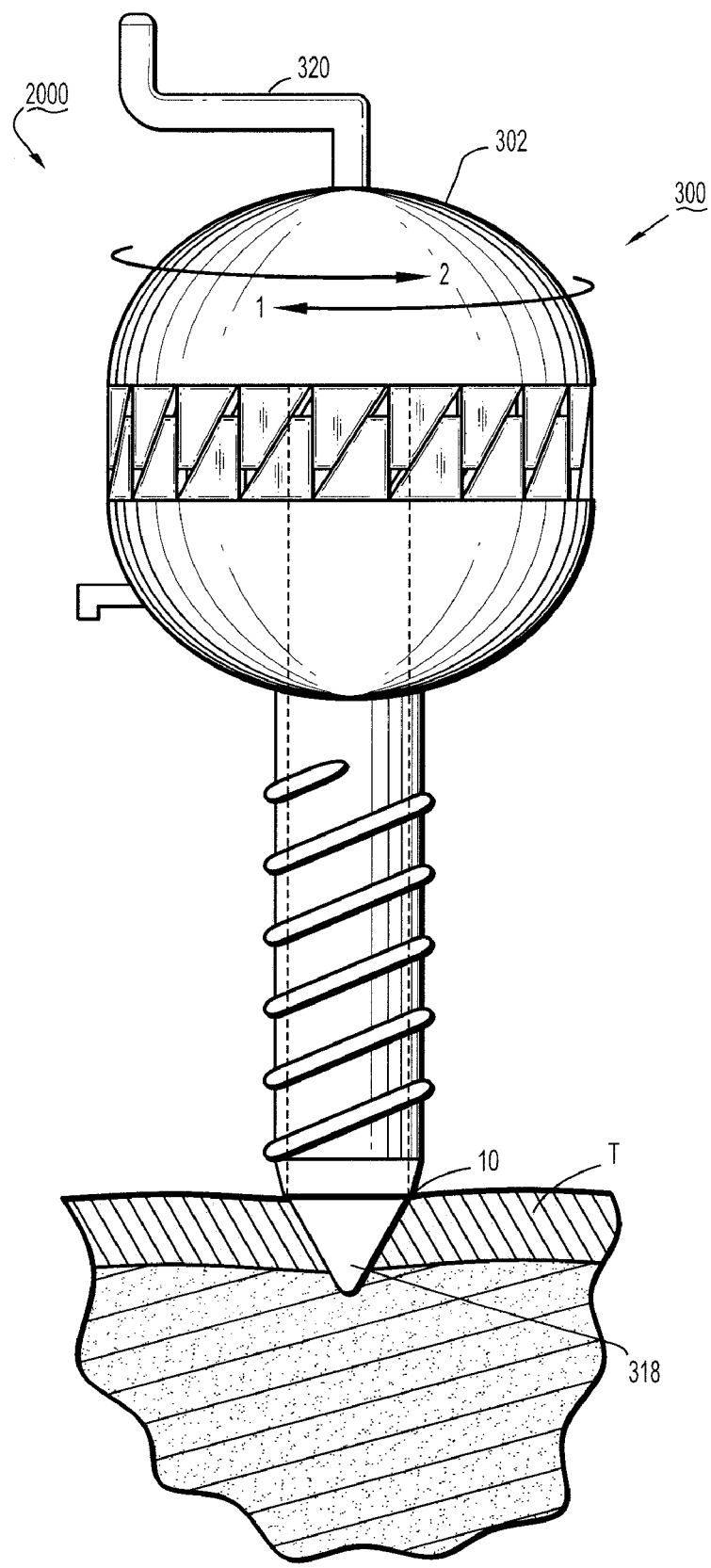
FIG. 7 is a side view of an alternate embodiment of the surgical access system of FIG. 1 including a handle connected to the obturator assembly.

Referring now to FIG. 7, another embodiment of the surgical access system, referred to generally by reference number 2000 will be described. The surgical access system 2000 is substantially similar to the surgical access system 1000 discussed above with respect to FIGS. 1-6, and accordingly, will only be discussed with respect to its differences therefrom.

As seen in FIG. 7, the obturator assembly 300 includes a handle 320 connected to the obturator housing 302 to facilitate rotation thereof. The handle 320 may be integrally formed with the obturator housing 302, as illustrated in FIG. 7, or alternatively, the handle 320 may be releasably connectable with the obturator housing 302 through the employ of corresponding attachment and receipt structure.

After positioning the distal end 318 of the obturator assembly 300 within the tissue tract 10 formed in the tissue "T", the clinician uses the handle 320 to rotate the obturator assembly 300, either alternating between the directions indicated by arrows 1 and 2, or continuously in the direction of arrow 1, as described above with respect to FIGS. 1-6.

Figure 8:
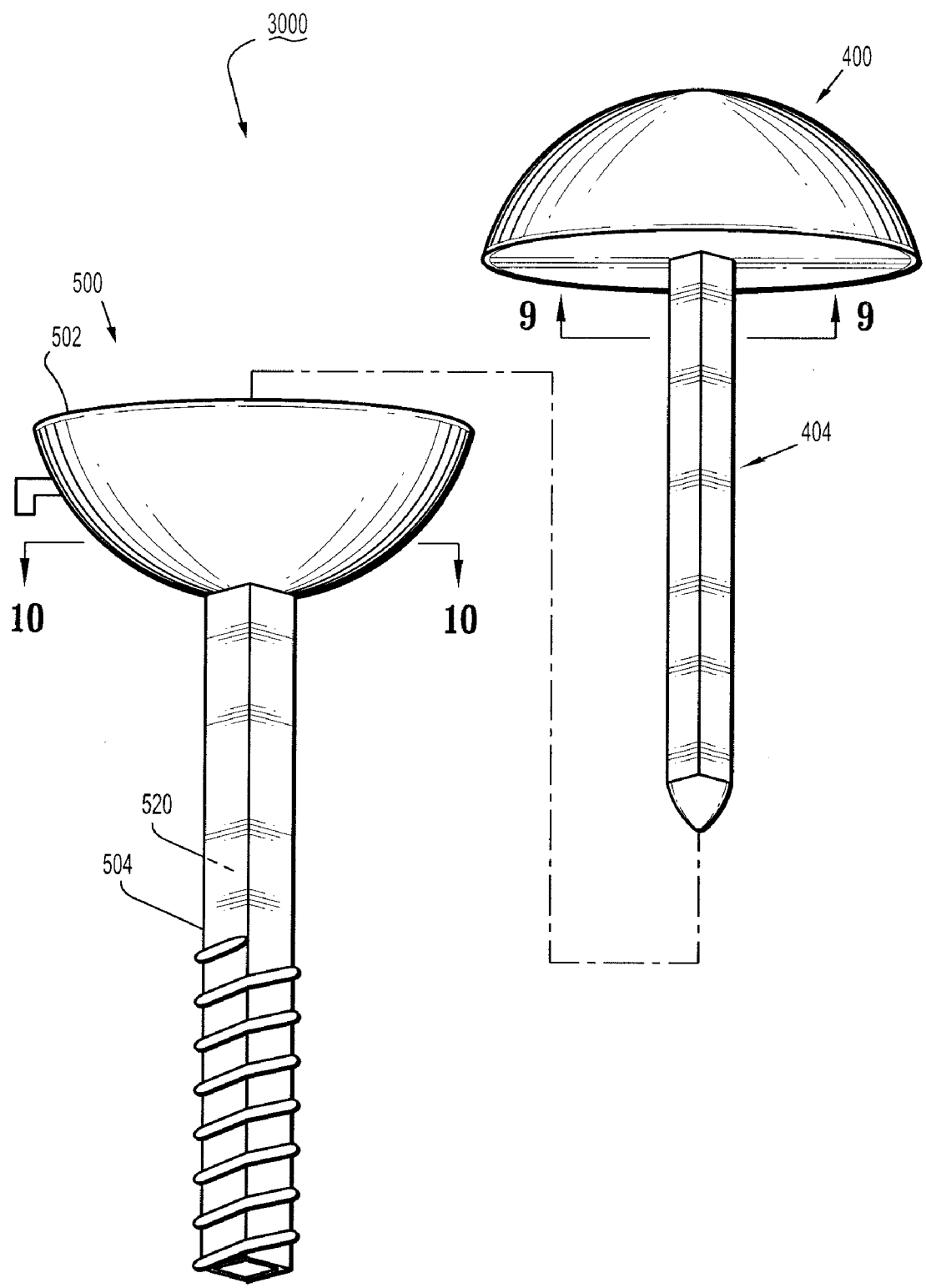
FIG. 8 is a side view of another embodiment of the surgical access system of FIG. 1 shown in a disassembled condition.
Figure 9:
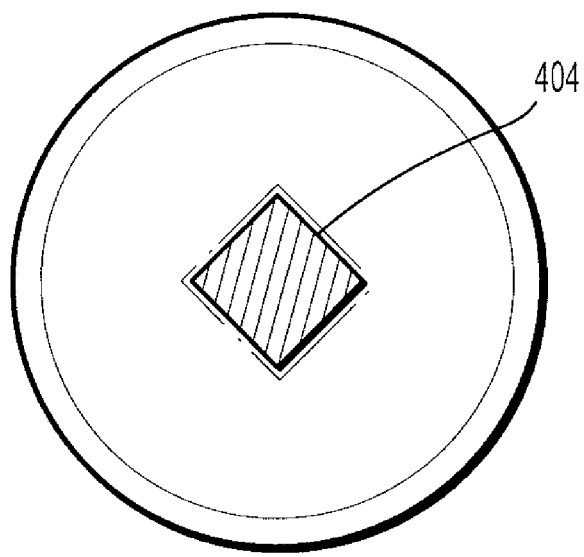
FIG. 9 is a bottom view of the obturator assembly seen in FIG. 8 taken through line 9-9.
Figure 10:
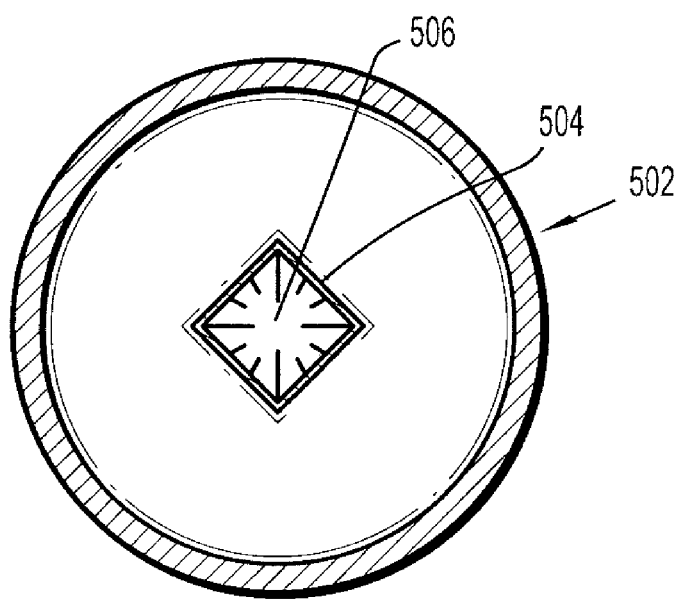
FIG. 10 is a top view of the cannula assembly seen in FIG. 8 taken through line 10-10.

Referring now to FIGS. 8-10, another embodiment of the surgical access system, referred to generally by reference number 3000 will be described. The surgical access system 3000 is substantially similar to the surgical access system 1000 discussed above with respect to FIGS. 1-6, and accordingly, will only be discussed with respect to its differences therefrom.

In contrast to the obturator assembly 100 seen in FIGS. 1 and 4, for example, in which the obturator sleeve 104 defines a substantially circular cross-sectional configuration along its entire length, at least a portion of the obturator sleeve 404 of the obturator assembly 400 defines a non-circular, e.g., polygonal, cross-sectional configuration. In the particular embodiment illustrated in FIGS. 8 and 9, the obturator sleeve 404 defines a square cross-sectional configuration along its entire length. However, in alternate embodiments, only a portion of the obturator sleeve 404, e.g., a proximal portion thereof, may define the non-circular cross-sectional configuration. Additionally, in alternate embodiments, various other non-circular geometric configurations are contemplated for the sleeve 404, including but not limited to hexagonal and triangular configurations.

As seen in FIG. 10, the opening 506 extending through the cannula housing 502 of the cannula assembly 500 also defines a non-circular, e.g., polygonal, configuration that corresponds to the cross-sectional configuration defined by the obturator sleeve 404. As such, in the embodiment seen in FIGS. 8 and 10, the opening 506 extending thorough the cannula housing 502 defines a square configuration. Optionally, the lumen 520 extending through the cannula sleeve 504 may also define a non-circular, e.g., polygonal, configuration corresponding to that of the obturator sleeve 404. Upon insertion of the obturator assembly 400 into the cannula assembly 500, the corresponding configurations of the obturator sleeve 404 and the opening 506 substantially prevent rotation of the obturator assembly 400 relative to the cannula assembly 500. Accordingly, rotation of the obturator assembly 400 effectuates corresponding rotation of the cannula assembly 500, thereby obviating the need for the teeth 108, 210 respectively formed on the obturator and cannula assemblies 100, 200 of the surgical access system 1000 discussed above with respect to FIGS. 1-6.

Figure 11:
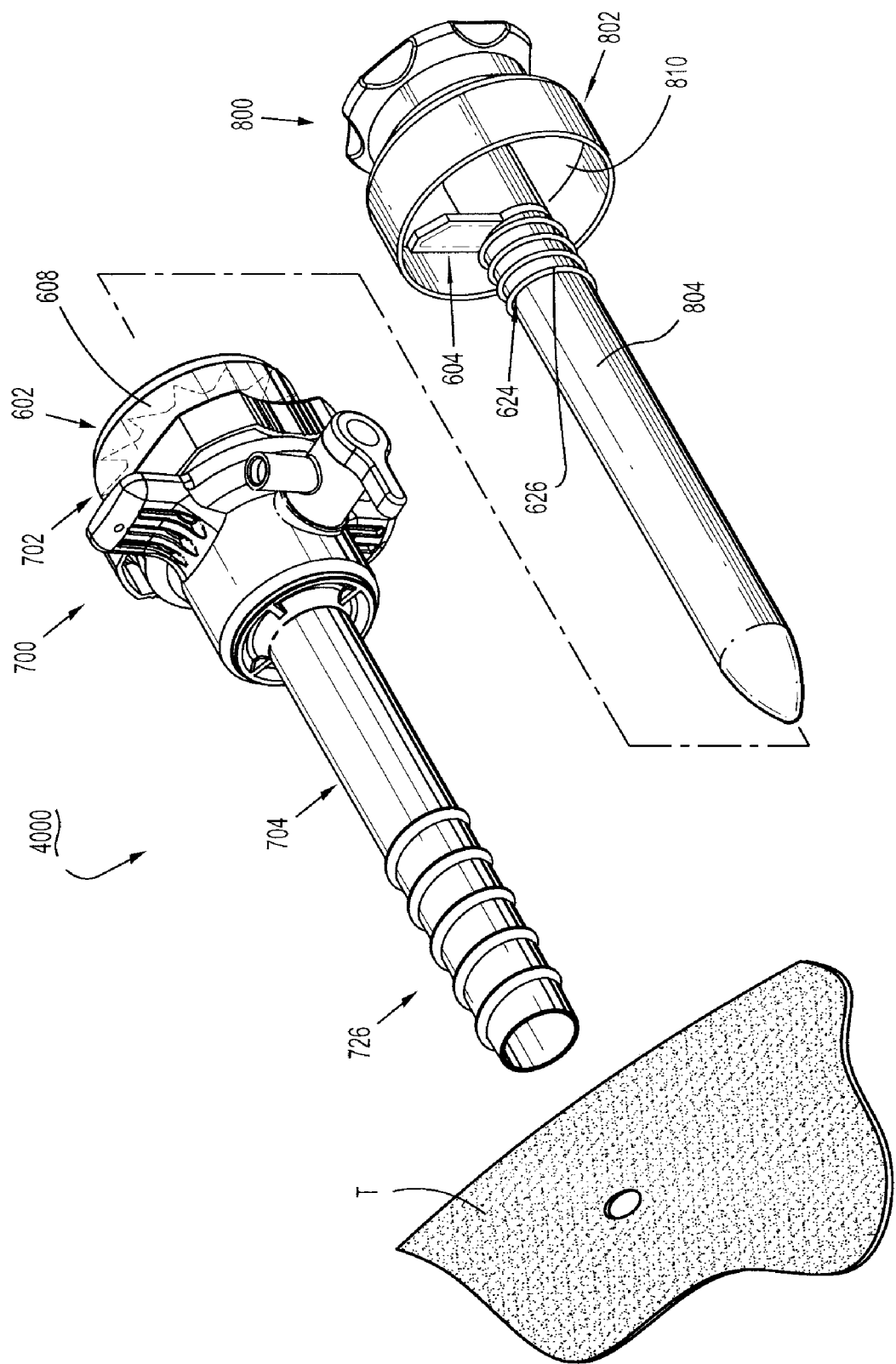
FIG. 11 is a perspective view of another embodiment of the surgical access system in accordance with the principles of the present disclosure shown in a disassembled condition and including a ratcheting mechanism including a rack associated with the obturator assembly that is engagable with a pawl associated with the obturator assembly.
Figure 12:
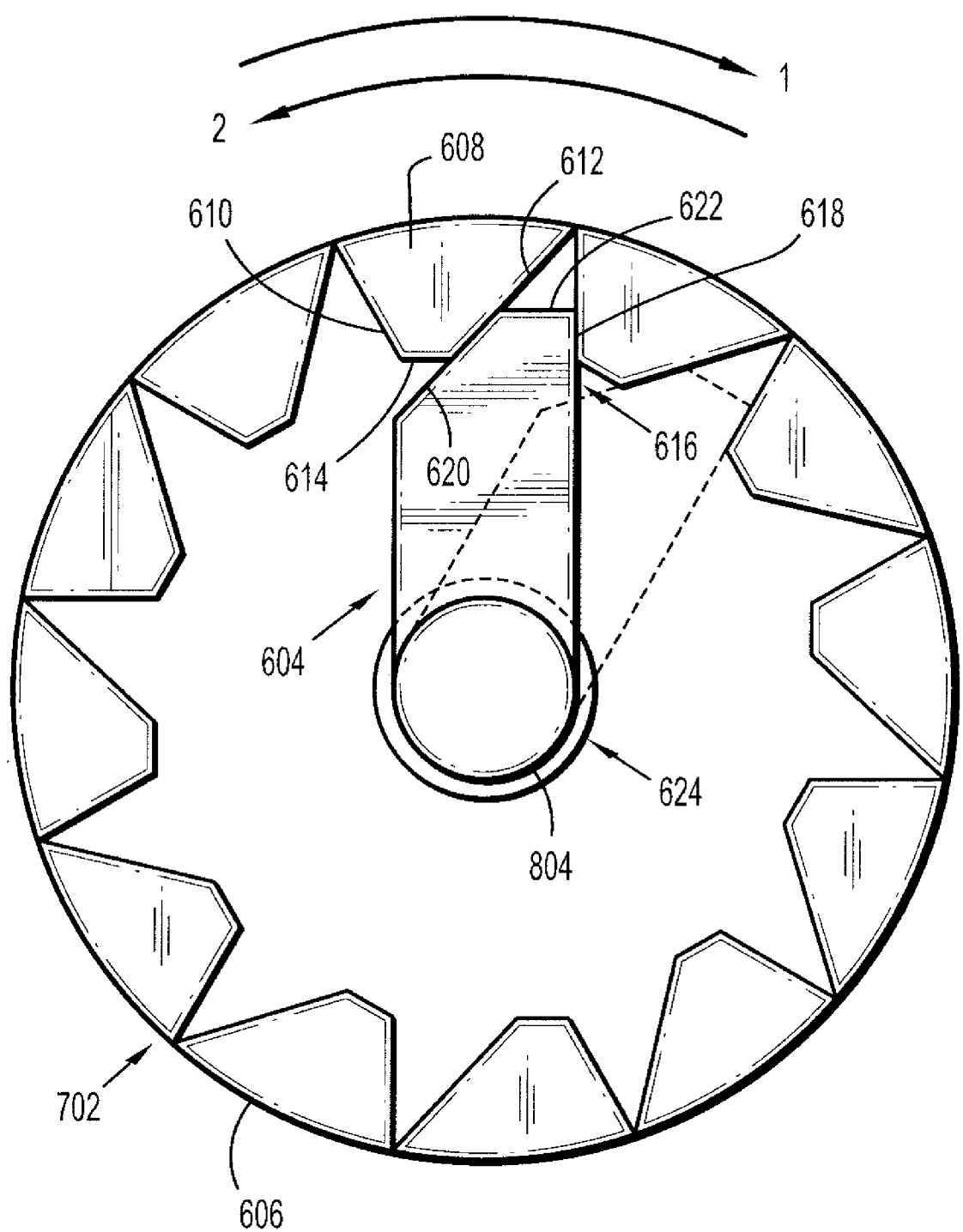
FIG. 12 is a top, cross-sectional view taken through the ratcheting mechanism upon assembly of the surgical access system seen in FIG. 11 illustrating the engagement of the rack and the pawl.

Referring now to FIGS. 11-12, still another embodiment of the surgical access system, referred to generally by reference number 4000 will be described. The surgical access system 4000 is substantially similar to the surgical access system 1000 discussed above with respect to FIGS. 1-6, and accordingly, the surgical access system 4000 will only be discussed with respect to its differences therefrom.

The surgical access system 4000 incorporates a ratcheting mechanism 600 including a rack 602 associated with the cannula assembly 700 and a pawl 604 associated with the obturator assembly 800. The rack 602 and the pawl 604 are engagable in the manner described below to facilitate selective engagement and disengagement of the obturator assembly 800 and the cannula assembly 700 comprising the surgical access system 4000.

In the embodiment of the ratcheting mechanism 600 discussed below with respect to FIGS. 11-12, the rack 602 is formed on an inner wall 606 of the cannula housing 702 and the pawl 604 is illustrated in mechanical cooperation with the obturator sleeve 804. However, it should be appreciated that the rack 602 and the pawl 604 may be positioned in any manner suitable to permit the engagement thereof. As an illustrative example, the present disclosure contemplates that the pawl 604 may alternatively be positioned on the distal wall 810 of the obturator housing 802.

The rack 602 includes a plurality of teeth 608 depending radially inward from the cannula housing 702, i.e., away from the inner wall 606 towards the opening (not shown) extending through the cannula housing 702. In the particular embodiment of the ratcheting mechanism 600 seen in FIGS. 11-12, each tooth 608 includes a first surface 610 and a second, chamfered surface 612 connected by an end surface 614. However, alternate configurations for the teeth 608 are also within the scope of the present disclosure. The first surface 610 extends radially inward from the inner wall 606 while the second surface 612 extends from the inner wall 606 such that an acute angle α is defined therewith.

The pawl 604 defines a radial portion 616 that includes a first surface 618 and a second, chamfered surface 620 connected by an end surface 622, each of which corresponds in configuration and dimensions to the respective first, second, and end surfaces 610, 612, 614 of the teeth 608 comprising the rack 602. The pawl 604 is in mechanical cooperation with a biasing member 624 to facilitate reciprocal displacement of the pawl 604 relative to the obturator sleeve 804 in the directions indicated by arrows 1 and 2. While the biasing member 624 is illustrated as a spring 626 disposed about the obturator sleeve 804, in alternate embodiments, the biasing mechanism 624 may constitute any mechanism suitable for the intended purpose of biasing the pawl 604 towards a normal position thereof, which can be seen in FIG. 12, positionable in any suitable location.

In the normal position, the first and second surfaces 618, 620 of the pawl 604 respectively engage the first and second surfaces 610, 612 of adjacent teeth 608. Due to this engagement, rotating the obturator assembly 800, and thus, the pawl 604 in one direction endeavors to displace the pawl 604 in the opposite direction. Specifically, rotating the obturator assembly 800 in the direction of arrow 1 endeavors to displace the pawl 604 in the direction of arrow 2, and rotating the obturator assembly 800, and thus, the pawl 604 in the direction of arrow 2 endeavors to displace the pawl 604 in the direction of arrow 1. However, displacement of the pawl 604 from the normal position in the direction of arrow 2 is substantially proscribed such that movement of the pawl 604 in the direction of arrow 2 is limited to movement facilitated by the influence of the biasing member 624 as the pawl 604 is returned to the normal position following displacement of the pawl 604 in the direction of arrow 1, as described in further detail below.

Prohibiting displacement of the pawl 604 from the normal position in the direction of arrow 2 prohibits relative rotation between the obturator assembly 800 and the cannula assembly 700 in the direction of arrow 1. Accordingly, rotating the obturator assembly 800, and thus, the pawl 604 in the direction of arrow 1 effectuates corresponding rotation of the cannula assembly 700 through the engagement of the pawl 604 with the teeth 608 of the rack 602. By contrast, displacement the pawl 604 in the direction of arrow 1 is unrestricted such that rotation of the obturator assembly 800 relative to the cannula assembly 700 in the direction of arrow 2 is permitted. As the obturator assembly 800, and thus, the pawl 604 is rotated in the direction of arrow 2, the second surface 612 of each tooth 608 traverses the second surface 620 of the pawl 604. This causes displacement of the pawl 604 in the direction of arrow 1 and allows the clinician to rotate the obturator assembly 800 in the direction of arrow 2 without causing corresponding rotation of the cannula assembly 700. Subsequently, the pawl 604 is urged back towards the normal position by the biasing member 624, thereby facilitating manipulation of the surgical access system 4000 in a ratcheting manner in which rotation of the obturator assembly 800 can be alternated between the directions indicated between arrows 1 and 2.

As the cannula assembly 700 is rotated in the direction of arrow 1, the threaded portion 726 of the cannula sleeve 704 engages the patient's tissue "T", causing advancement of the surgical access system 4000 therethrough, as discussed above with respect to FIGS. 1-6.

While the clinician may choose to manipulate the surgical access system 4000 in the ratcheting manner described above, alternating rotation of the obturator assembly 800 between the directions indicated by arrows 1 and 2, alternatively, the clinician may choose to simply rotate the obturator assembly 800, and thus, the cannula assembly 700 continuously in the direction of arrow 1.

Persons skilled in the art will understand that the systems and methods specifically described herein and illustrated in the accompanying drawings are intended to be construed as non-limiting, exemplary embodiments, and that the features illustrated or described in connection with one exemplary embodiment may be combined with the features of other embodiments. Additionally, one skilled in the art will appreciate further features and advantages of the disclosure based on the above-described embodiments. As such, the disclosure is not to be limited by what has been particularly shown and described, except as indicated by the appended claims.

What is claimed is:

1. A surgical access system comprising:
   a cannula assembly including first engagement structure and being adapted for removable positioning within a percutaneous tissue tract; and
   an obturator assembly removably positionable within the cannula assembly and including second engagement structure, the second engagement structure corresponding in configuration to the first engagement structure of the cannula assembly, the first and second engagement structure being configured and dimensioned to permit rotation of the obturator assembly relative to the cannula assembly in a first direction, and substantially inhibit rotation of the obturator assembly relative to the cannula assembly in a second direction opposite the first direction relative such that rotation of the obturator assembly in the second direction effectuates corresponding rotation of the cannula assembly to facilitate advancement of the cannula assembly through tissue.

2. The surgical access system of claim 1, wherein the cannula assembly includes a cannula housing and a cannula sleeve, and the obturator assembly includes an obturator housing and an obturator sleeve.

3. The surgical access system of claim 2, wherein the first engagement structure depends proximally from the cannula housing and the second engagement structure depends distally from the obturator housing.

4. The surgical access system of claim 2, wherein the cannula sleeve includes a threaded portion configured and dimensioned to engage the tissue as the cannula assembly is rotated in the second direction to thereby facilitate advancement of the cannula assembly through the tissue.

5. The surgical access system of claim 2, wherein the first engagement structure includes a rack and the second engagement structure includes a pawl, the pawl being configured and dimensioned for engagement with the rack to permit ratcheting movement of the obturator assembly relative to the cannula assembly.

6. The surgical access system of claim 5, wherein the rack is positioned on an inner wall of the cannula housing.

7. The surgical access system of claim 5, wherein the pawl is in mechanical cooperation with the obturator sleeve.

8. The surgical access system of claim 5, wherein the rack includes a plurality of teeth each having a first planar surface and a first chamfered surface and the pawl includes a second planar surface and a second chamfered surface.

9. The surgical access system of claim 8, wherein the plurality of teeth depend inwardly from the cannula housing.

10. The surgical access system of claim 8, wherein the first planar surface of the rack is configured and dimensioned to engage the second planar surface of the pawl.

11. The surgical access system of claim 10, wherein the first chamfered surface of the rack is configured and dimensioned to engage the second chamfered surface of the pawl.

12. The surgical access system of claim 11, wherein the obturator assembly further includes a biasing mechanism connected to the pawl to facilitate reciprocal movement of the pawl in the first and second directions.

13. The surgical access system of claim 1, wherein the first engagement structure includes a first plurality of teeth and the second engagement structure includes a second plurality of teeth, the first plurality of teeth being configured and dimensioned to engage the second plurality of teeth in an interlocking arrangement.

14. The surgical access system of claim 13, wherein the first plurality of teeth each include a first inner surface and a first outer surface, and the second plurality of teeth each include a second inner surface and a second outer surface.

15. The surgical access system of claim 14, wherein the first outer surface is configured and dimensioned to engage the second inner surface.

16. The surgical access system of claim 15, wherein the first outer surface and the second inner surface are each substantially planar.

17. The surgical access system of claim 14, wherein the first inner surface is configured and dimensioned to engage the second outer surface.

18. The surgical access system of claim 17, wherein the first inner surface and the second outer surface are correspondingly chamfered.

19. The surgical access system of claim 1, wherein the obturator assembly includes a handle configured and dimensioned for manual engagement to facilitate rotation of the obturator assembly.

20. A method of establishing percutaneous access to a surgical worksite comprising the steps of:
   positioning a cannula assembly within a tissue tract;
   positioning an obturator assembly within the cannula assembly to cause mechanical association of corresponding engagement structure included on the obturator assembly and the cannula assembly, whereby rotation of the obturator assembly relative to the cannula assembly is permitted in a first direction, and rotation of the obturator assembly relative to the cannula assembly is substantially inhibited in a second direction opposite the first direction such that rotation of the obturator assembly in the second direction effectuates corresponding rotation of the cannula assembly to facilitate advancement of the cannula assembly through tissue; and
   rotating the obturator assembly in the second direction.

21. A surgical access system comprising:
   a cannula assembly configured and dimensioned for removable positioning within a percutaneous tissue tract; and
   an obturator assembly configured and dimensioned for insertion into the cannula assembly, the cannula assembly and the obturator assembly being configured and dimensioned such that the obturator assembly is rotatable relative to the cannula assembly in a first direction, and substantially prevented from rotation relative to the cannula assembly in a second direction, whereby rotation of the obturator assembly in the second direction effectuates corresponding rotation of the cannula assembly to facilitate advancement of the cannula assembly through tissue.

22. The surgical access system of claim 21, wherein the cannula assembly includes a first plurality of teeth, and the obturator assembly includes a second plurality of teeth configured and dimensioned to engage the first plurality of teeth in an interlocking arrangement.

23. The surgical access system of claim 22, wherein the first plurality of teeth and the second plurality of teeth include corresponding chamfered portions.

* * * * *